(12) United States Patent
Ding

(10) Patent No.: US 6,624,157 B2
(45) Date of Patent: Sep. 23, 2003

(54) THIADIOXOBENZODIAZEPINE INHIBITORS OF FARNESYL PROTEIN TRANSFERASE

(75) Inventor: Charles Z. Ding, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/769,809

(22) Filed: Jan. 26, 2001

(65) Prior Publication Data

US 2001/0039273 A1 Nov. 8, 2001

Related U.S. Application Data

(63) Continuation of application No. 08/887,183, filed on Jul. 2, 1997, now abandoned.
(60) Provisional application No. 60/021,786, filed on Jul. 15, 1996.

(51) Int. Cl.$^7$ ..................... A61K 31/551; C07D 417/06
(52) U.S. Cl. .................. 514/211.06; 514/211.07; 514/211.08; 540/489; 540/545
(58) Field of Search .................. 540/489, 545; 514/211.06, 211.07, 211.08

(56) References Cited

U.S. PATENT DOCUMENTS

| | | | |
|---|---|---|---|
| 5,036,065 A | | 7/1991 | Ogawa et al. ............... 514/211 |
| 6,156,746 A | * | 12/2000 | Leftheris et al. ........ 514/211.06 |

FOREIGN PATENT DOCUMENTS

| | | |
|---|---|---|
| JP | 02/138272 | 5/1990 |
| WO | WO 94/26723 | 11/1994 |
| WO | WO 97/30992 | 8/1997 |

OTHER PUBLICATIONS

Artico, M. et al., Bioorg. Med. Chem., vol. 4, No. 6, 837–850 (1996).
Ding, C. Z. et al., J. Med. Chem., vol. 42, No. 25, 5241–5253 (1999).
James, G. L. et al., Science, vol. 260, 1937–1942 (Jun. 25, 1993).
Owawa, K. et al., Chem. Pharm. Bull., vol. 40, No. 9, 2442–2447 (1992).

* cited by examiner

Primary Examiner—Richard L. Raymond
(74) Attorney, Agent, or Firm—Maureen S. Gibbons

(57) ABSTRACT

Inhibition of farnesyl transferase, which is an enzyme involved in ras oncogene expression, is effected by compounds of the formulas

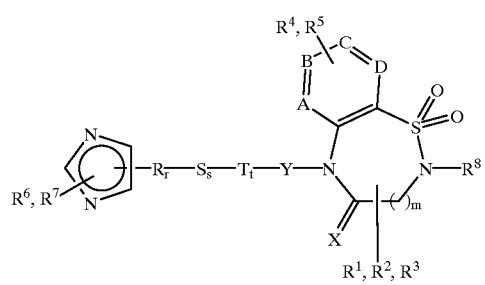

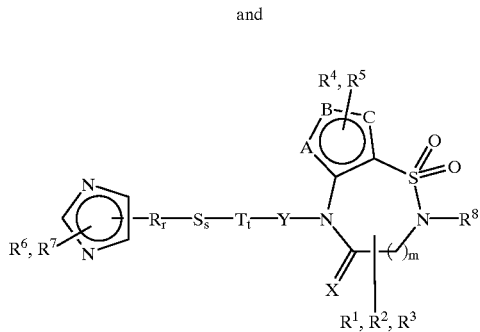

and their enantiomers, diastereomers, and their pharmaceutically acceptable salts, including prodrugs and solvates thereof wherein:

r, s and t are 0 or 1;

m=0, 1, 2;

p is 0, 1 or 2;

X is selected from the group consisting of oxygen, hydrogen or $R^1$, $R^2$, $R^3$;

Y is selected from the group consisting of $CHR^9$, $SO_2$, CO, $CO_2$, O, $NR^{10}$, $SO_2NR^{11}$ and $CONR^{12}$;

$R^6$, $R^7$, $R^9$, $R^{10}$, $R^{11}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are selected from the group consisting of hydrogen, lower alkyl or substituted alkyl;

$R^4$, $R^5$ are selected from the group consisting of hydrogen, halo, nitro, cyano and U-$R^{13}$;

$R^{12}$ is selected from the group consisting of hydrogen, lower alkyl, aryl, substituted alkyl or aryl;

U is selected from the group consisting of sulfur, oxygen, $NR^{14}$, CO, SO, $SO_2$, $CO_2$, $NR^{15}CO_2$, $NR^{16}CONR^{17}$, $NR^{19}SO_2$, $NR^{19}SO_2NR^{20}$, $SO_2NR^{21}$, $NR^{22}CO$, $CONR^{23}$, $PO_2R^{24}$ and $PO_3R^{25}$ or U is absent;

$R^1$, $R^2$, $R^3$, $R^8$ and $R^{13}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

R, S and T are selected from the group consisting of $CH_2$, CO and $CH(CH_2)_pQ$ wherein Q is $NR^{26}R^{27}$ or $OR^{28}$;

and A, B, C and D are carbon, oxygen, sulfur or nitrogen. with the proviso that $R^{13}$ may be hydrogen except when U is SO, $SO_2$, $NR^{15}CO_2$ or $NR^{18}SO_2$.

7 Claims, No Drawings

THIADIOXOBENZODIAZEPINE INHIBITORS OF FARNESYL PROTEIN TRANSFERASE

This is a continuation of Ser. No. 08/887,183, Jul. 2, 1997, abandoned, which claims the benefit of Ser. No. 60/021,786, Jul.15, 1996.

FIELD OF THE INVENTION

This invention relates to compounds that inhibit farnesyl protein transferase and ras protein farnesylation, thereby making them useful as anticancer agents. The compounds are also useful in the treatment of diseases, other than cancer, associated with signal transduction pathways operating through ras and those associated with CAAX-containing proteins other than ras that are also post-translationally modified by the enzyme farnesyl protein transferase. The compounds may also act as inhibitors of other prenyl transferases, and thus be effective in the treatment of diseases associated with other prenyl modifications of proteins.

BACKGROUND OF THE INVENTION

The mammalian ras gene family comprises three genes, H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division. The transforming activity of ras is dependent on localization of the protein to plasma membranes. This membrane binding occurs via a series of posttranslational modifications of the cytosolic ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-Aaa1-Aaa2-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

BRIEF DESCRIPTION OF THE INVENTION

In accordance with the present invention, compounds of the formulas I and II

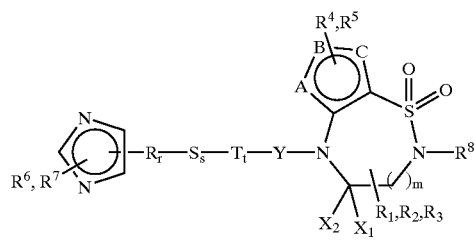

their enantiomers, diastereomers, and pharmaceutically acceptable salts, prodrugs and solvates thereof inhibit farnesyl protein transferase which is an enzyme involved in ras oncogene expression. In formulas I–II and throughout their specification, the above symbols are defined as follows:

r, s and t are 0 or 1;

m=0, 1, 2;

p is 0, 1 or 2;

$X_1$ and $X_2$ are, independently, selected from the group consisting of oxygen, hydrogen, $R^1$, $R^2$, or $R^3$;

Y is selected from the group consisting of $CHR^9$, $SO_2$, $CO$, $CO_2$, $O$, $NR^{10}$, $SO_2NR^{11}$ AND $CONR^{12}$; $R^6$, $R^7$, $R^9$, $R^{10}$, $R^{11}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are selected from the group consisting of hydrogen, lower alkyl or substituted alkyl;

$R^4$, $R^5$ are selected from the group consisting of hydrogen, halo, nitro, cyano and $U-R^{13}$; $R^4$ and $R^5$ may join together to form a carbocyclic or heterocyclic ring;

$R^{12}$ is selected from the group consisting of hydrogen, lower alkyl, aryl, substituted alkyl or aryl;

U is selected from the group consisting of sulfur, oxygen, $NR^{14}$, $CO$, $SO$, $SO_2$, $CO_2$, $NR^{15}CO_2$, $NR^{16}CONR^{17}$, $NR^{18}SO_2NR^{19}SO_2NR^{20}$, $SO_2NR^{21}$, $NR^{22}CO$, $CONR^{23}$, $PO_2R^{24}$ and $PO_2R^{25}$ or U is absent;

$R^1$, $R^2$, $R^3$, $R^8$ and $R^{13}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

R, S and T are selected from the group consisting of $CH_2$, CO and $CH(CH_2)_pQ$ wherein Q is $NR^{26}R^{27}$ or $OR^{28}$;

and A, B, C and D are carbon, oxygen, sulfur or nitrogen, with the proviso that $R^{13}$ may be hydrogen except when U is SO, $SO_2$, $NR^{15}CO_2$ or $NR^{18}SO_2$.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, alkanoyl, alkanoyloxy, amino, alkylamino, aralkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to a optionally substituted, saturated cyclic hydrocarbon ring systems, preferably containing 1 to 3 rings and 3 to 7 carbons per ring which may be further fused with an unsaturated C3–C7 carbocyclic ring.

Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", heterocyclic and "heterocycle" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl) or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocycles, such as, epoxides and aziridines.

The term "heteroatoms" shall include oxygen, sulfur and nitrogen.

The 'ABCD' fused ring to the diazepine ring may be monocyclic or bicyclic, e.g. naphthyl or quinolyl in nature.

The compounds of formulas I–II may form salts which are also within the scope of this invention. Pharmaceutically acceptable (i.e. non-toxic, physiologically acceptable) salts are preferred, although other salts are also useful, e.g, in isolating or purifying the compounds of this invention.

The compounds of formulas I–II may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compounds I–II with the desired ion in a medium in which the salt precipitates or in an aqueous medium followed by evaporation. Other salts can be formed as known to those skilled in the art.

The compounds for formulas I–II may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds I–II in an equivalent amount of the acid in a medium in which the salt precipitates or in an aqueous medium followed by evaporation. In addition, zwitterions ("inner salts") may be formed.

Compounds of the formulas I–II may also have prodrug forms. Any compound that will be converted in vivo to provide the bioactive agent (i.e., the compound for formulas I–II) is a prodrug within the scope and spirit of the invention.

For example compounds of the formulas I–II may be a carboxylate ester moiety. The carboxylate ester may be conveniently formed by esterifying any of the carboxylic acid functionalities found on the disclosed ring structure(s).

Various forms of prodrugs are well known in the art. For examples of such prodrug derivatives, see:
a) *Design of Prodrugs,* edited by H. Bundgaard, (Elsevier, 1985) and *Methods in Enzymology,* Vol.42, p. 309–396, edited by K. Widder, et al. (Academic Press, 1985);
b) *A Textbook of Drug Design and Development,* edited by KrosgaardLarsen and H. Bundgaard, Chapter 5, "Design and Application of Prodrugs," by H. Bundgaard, p. 113–191 (1991);
c) H. Bundgaard, *Advanced Drug Delivery Reviews,* 8, 1–38 (1992);
d) H. Bundgaard, et al., *Journal of Pharmaceutical Sciences,* 77, 285 (1988); and
e) N. Kakeya, et al., *Chem Phar Bull,* 32, 692 (1984).

It should further be understood that solvates (e.g., hydrates) of the compounds of formulas I–II are also with the scope of the present invention. Methods of solvation are generally known in the art.

Preferred Moieties

For compounds of the present invention, the following moieties are preferred:

Compounds of formulas I and II wherein "ABCD" and "ABC" are a carbocyclic ring.

More preferred are compounds of formula I wherein m is one and "ABCD" is a carbocyclic ring, e.g. benzo.

Use and Utility

The compounds of formulas I–II are inhibitors of S-farnesyl protein transferase. They are thus useful in the treatment of a variety of cancers, including (but not limited to) the following;

carcinoma, including that of the bladder, breast, colon, kidney, liver, lung, including small cell lung cancer, ovary, prostate, testes, pancreas, esophagus, stomach, gall bladder, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias, myelodysplastic syndrome and promyelocytic leukemia;

tumors of the central and peripheral nervous system, including astrocytoma, neuroblastoma, glioma, and schwannomas;

tumors of mesenchymal origin, including fibrosarcoma, rhabdomyoscarcoma, and osteosarcoma;

other tumors, including melanoma, xenoderma pigmentosum, keratoactanthoma, seminoma, thyroid follicular cancer and teratocarcinoma.

The compounds of formulas I–II are especially useful in treatment of tumors having a high incidence of ras involvement, such as colon, lung, and pancreatic tumors and in tumors in which a prenyl transferase contributes to tumor maintenance, tumor growth or tumor development. By the administration of a composition having one (or a combination) of the compounds of this invention, development of tumors in a mammalian host is reduced, or tumor burden is reduced, or tumor regression is produced.

Compounds of formulas I–II may also inhibit tumor angiogenesis, thereby affecting the growth of tumors. Such anti-angiogenesis properties of the compounds of formulas I–II may also be useful in the treatment of certain forms of blindness related to retinal vascularization.

Compounds of formulas I–II may also be useful in the treatment of diseases other than cancer that may be associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation, polycystic kidney disease and endotoxic shock. Compounds I–II may be useful as anti-fungal agents.

Compounds of formula I–II may induce or inhibit apoptosis, a physiological cell death process critical for normal development and homeostasis. Alterations of apoptotic pathways contribute to the pathogenesis of a variety of human diseases. Compounds of formula I–II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpes virus, pox virus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

Compounds of formulas I–II may also be useful in the treatment of diseases associated with farnesyl transferase substrates other than ras (e.g., nuclear lamins, transducin, rhodopsin kinase, cGMP phosphodiesterase, TC21, phosphorylase kinase, Rap2, RhoB, RhoE, PRL1) that are also post-translationally modified by the enzyme farnesyl protein transferase.

Compounds of formulas I–II may also act as inhibitors of other prenyl transferases (e.g., geranylgeranyl transferase I and II), and thus be effective in the treatment of diseases associated with to other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., *Science*, 256, 1331 (1992)].

The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formulas I–II may be used sequentially with known anticancer or cytotoxic agents and treatment, including radiation when a combination formulation is inappropriate. Suitable cytotoxic agents which may be used in combination with the compounds of the present invention include the taxanes, e.g. paclitaxel, docetaxel or derivatives thereof; camptothecin derivatives e.g. topotecon or CPT-11; gemcitabine; platinum compounds e.g. cisplatin or carboplatin; telomerase inhibitors; various alkylating agents and tubulin stabilizing agents, e.g. epothilones among others.

Farnesyl transferase assays were performed as described in V. Manne et al., Drug Development Research, 34, 121–137, (1995). The compounds of Examples 1–50 inhibited farnesyl transferase with IC50 values between 0.1 nM and 100 $\mu$M.

The compounds of this invention may be formulated with a pharmaceutical vehicle or diluent for oral, intravenous, intraperitoneal, subcutaneous, intraabdominal, intramuscular, rectal, vaginal or topical administration. Oral administration may involve the use of slow release formulations, such as biodegradable polymers or prodrugs. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 400 mg/kg/day, in a single dose or in 2 to 4 divided doses.

Scheme 1

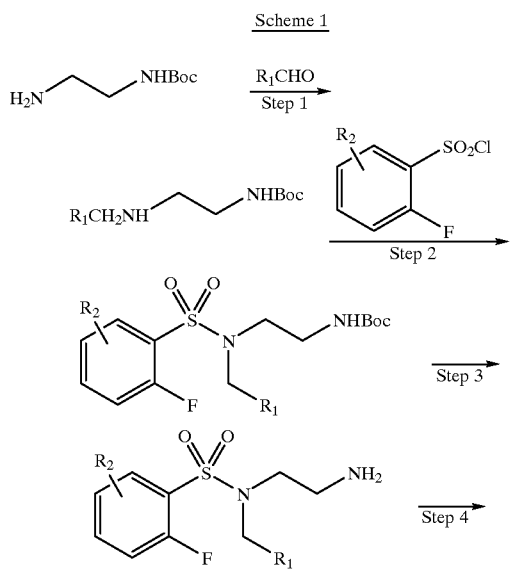

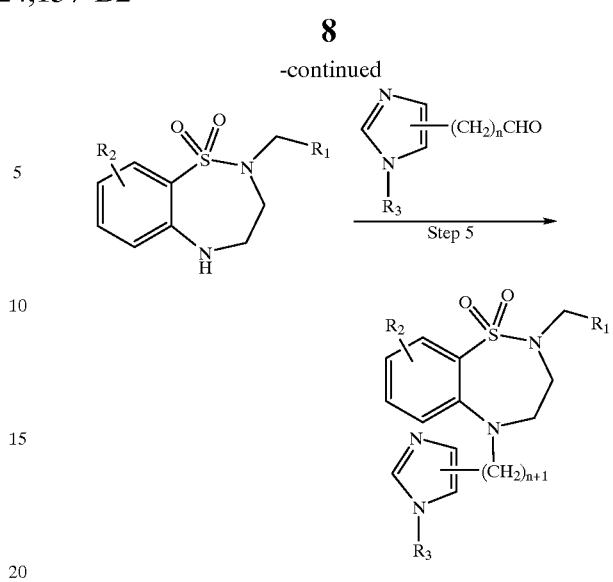

wherein $R_1$ is selected from arylalkyl, aryl, substituted aryl, heteroaryl; $R_2$ is selected from hydrogen, bromine, CN, alkyl or aryl; $R_3$ is selected from H, alkyl, subtituted alkyl, arylalkyl.

Step 1

A mono-protected ethylenediamine derivative is reductively alkylated with an aldehyde and a reducing agent such as NaCNBH$_3$ or Na(OAc)$_3$BH in an alcoholic solvent such as methanol in the presence of an acid such as acetic acid at from 0° C. to room temperature.

Step 2

The resulting mono-protected ethylenediamine derivative is sulfonylated with a 2-halo-arylsulfonyl chloride in a mixed aqueous/organic solvent system such as aqueous NaOH/methylene chloride at from 0° C. to room temperature.

Step 3

The amine protecting group is removed (e.g., Boc by an acid such as TFA in an organic solvent such as methylene chloride).

Step 4

The resulting compound is cyclized by heating in an organic solvent such as DMF in the presence of a base such as K$_2$CO$_3$ at from 50° C. to 100° C.

Step 5

The resulting compound is reductively alkylated with an imidazole containing aldehyde and a reducing agent such as NaCNBH$_3$ or Na(OAc)$_3$BH in an organic solvent such as dichloroethane or DMF in the presence of an acid such as acetic acid at from 0° C. to room temperature.

Scheme 2

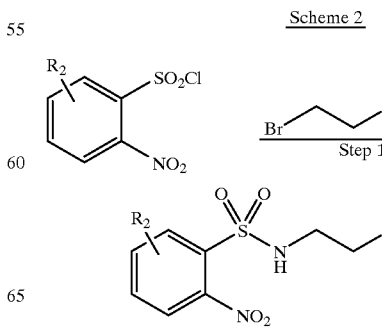

-continued

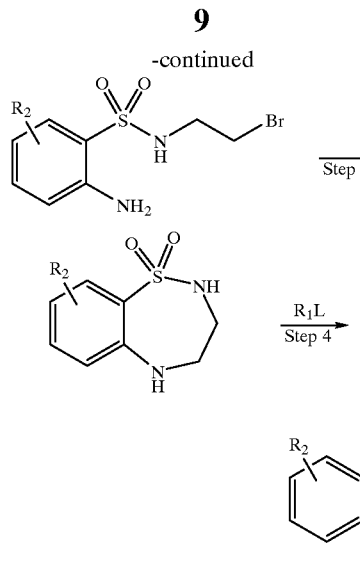

wherein $R_1$ is selected from substituted alkyl, arylalkyl, aryl, substituted aryl, heteroaryl and $R_2$ is selected from hydrogen, amino, substituted amino, halo, cyano, alkyl, substituted alkyl, aryl, heteroaryl or the combination of these groups.

Step 1

A 2-haloethylamine is sulfonylated with a 2-nitroarylsulfonyl chloride in a mixed aqueous/organic solvent system such as aqueous $NaHCO_3$/methylene chloride at from 0° C. to room temperature.

Step 2

The nitro group of the resulting compound is reduced to an amine, e.g., with $SnCl_2$ in an organic solvent such as ethyl acetate at room temperature.

Step 3

(a) The resulting aniline derivative is cyclized by heating in an alcoholic solvent such as ethanol.

(b) The compound where $R_2$ is bromo can be prepared by treatment of the compound where $R_2$ is H with bromine in a mixed organic solvent system such as DMF/acetic acid at room temperature.

Step 4

(a) The resulting compound is alkylated by $R_1$-L (where L is a leaving group such as a halide or a sulfonate) in an organic solvent system such as DMF in the presence of a base such as $K_2CO_3$ and a catalyst such as 18-crown-6 at from room temperature to 60° C.

(b) Where $R_1$ is aryl or heteroaryl, the reaction is performed in a suitable solvent such as collidine in the presence of a copper compound such as copper oxide at from 100° C. to 170° C.

(c) The compound where $R_1$ is oxadiazolylaryl is prepared from the compound where $R_1$ is alkoxycarbonylaryl by reaction with a N-hydroxyamidine derivative in a suitable solvent such as DMF in the presence of a base such as NaH at from 0° C. to 100° C.

(d) The compound where $R_2$ is bromo is prepared by treatment of the compound with a brominating reagent such as bromine in a mixed organic solvent system such as DMF/acetic acid, or tetrabutylammonium tribromide in chloroform at from 0° C. to room temperature. The compound where $R_2$ is aryl is prepared by reaction of the bromo derivative with an aryl metal derivative such as phenylboronic acid in, for example, a deoxygenated mixed aqueous/organic solvent system such as aqueous $NaHCO_3$/toluene in the presence of a palladium catalyst such as tetrakis (triphenylphosphine)-palladium at from room temperature to 100° C. This arylation reaction may also be performed in Step 3 of Scheme 2.

(e) The compound where $R_2$ is cyano group is prepared by treatment of the compound where $R_2$ is bromide with a metal cyanide such as copper cyanide in a suitable solvent such as NMP at an elevated temperature such as 180° C.

(f) The compound where $R_2$ is $R_4CONHCH_2$ is prepared from the compound where $R_2$ is CN by reduction with, for example, lithium aluminum hydride followed by acylation under standard conditions. The resulting compound is reductively alkylated as described in Step 5 of Scheme 1 to give a desired compound of formula I.

Scheme 3

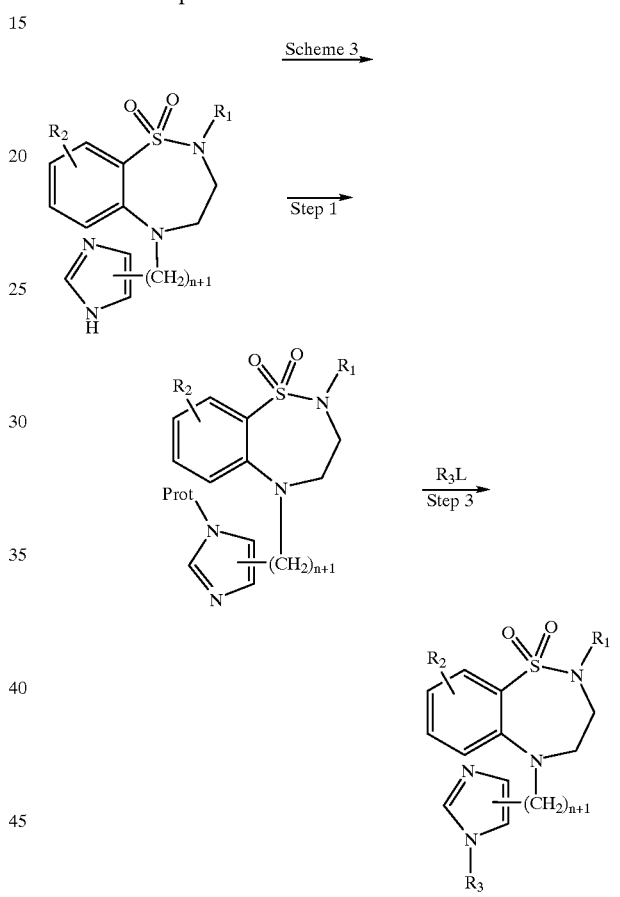

wherein $R_1$ is selected from substituted alkyl, arylalkyl, aryl, substituted aryl, heteroaryl; $R_2$ is selected from hydrogen, amino, substituted amino, halo, cyano, alkyl, substituted alkyl, aryl, heteroaryl or the combination of these groups; $R_3$ is selected from H, alkyl, subtituted alkyl, arylalkyl.

Step 1

An example is protected on the imidazole nitrogen, e.g., with trityl by treatment with triphenylmethylchlorde in an organic solvent such as pyridine at from 0° C. to room temperature.

Step 2

The resulting compound is alkylated with $R_3L$ (where L is a leaving group such as a halide or a sulfonate) in an organic solvent system such as DMF in the presence of a base such as diisopropylethylamine. Deprotection, e.g., with TFA and triethylsilane at from 0° C. to room temperature affords a target compound of formula I.

Scheme 4

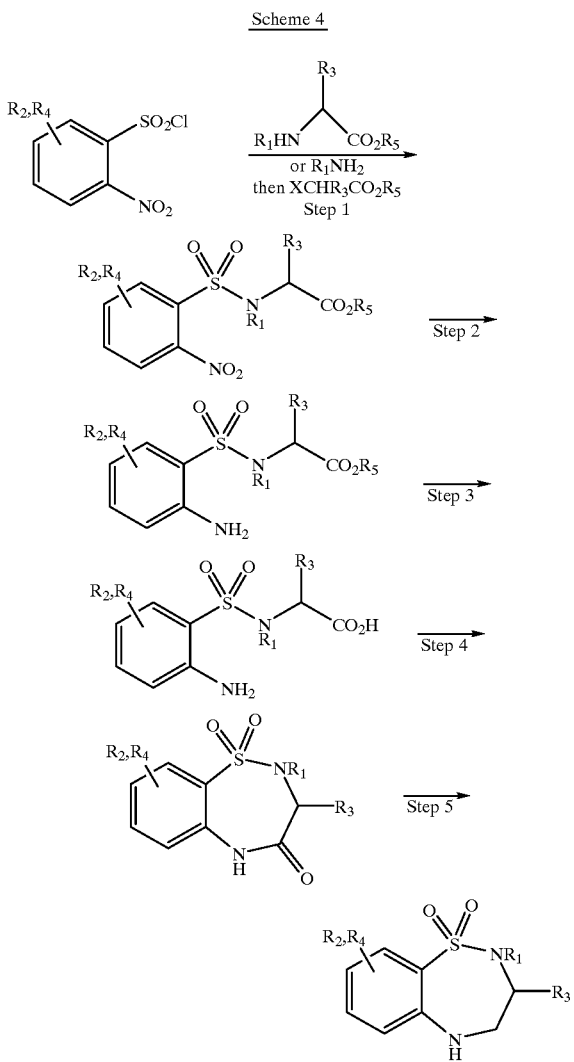

wherein $R_1$ is selected from H, substituted alkyl, arylalkyl, aryl, heteroaryl; $R_2$ and $R_4$ are selected from H, halo, $NO_2$, $NH_2$, CN, alkyl, substituted alkyl, arylalkyl, alkoxy and substituted amino and $R_2$ and $R_4$ may together form a carbocyclic or heterocyclic ring; $R_3$ is selected from H, substituted alkyl, arylalkyl.

Step 1

An amino acid ester with an optional nitrogen substitutent is sulfonylated with a 2-nitro-arylsulfonyl chloride in a mixed aqueous/organic solvent system such as aqueous $NaHCO_3$/methylene chloride at from 0° C. to room temperature. Alternatively, an amine is sulfonylated with a 2-nitro-benzenesulfonyl chloride, followed by alkylation of the resultant sulfonamide with a haloalkylester such as ethyl bromoacetate.

Step 2

(a) The nitro group of the resulting compound is reduced to an amine as in Step 2 of Scheme 2. If $R_2$ is a nitro group, that group is also reduced to an amine.

(b) If $R_1$ is H, the sulfonamide nitrogen can be alkylated at this step as described in Step 4 of Scheme 2.

Step 3

The carboxylic ester is converted to the carboxylic acid with a base such as lithium hydroxide in a mixed aqueous organic solvent such as $THF-H_2O-MeOH$ at room temperature.

Step 4

(a) The resultant carboxylic acid is cyclized with a dehydrating agent such as Bop chloride in an organic solvent such as DMF in the presence of a base such as diisopropylethylamine at from 0° C. to room temperature.

(b) If $R_2$ is an amine, it may be reductively alkylated with an aldehyde such as formadehyde in the presence of a reducing agent such as sodium cyanoborohydride. In addition, the amine group may be converted to a bromide by treatment with a nitrosating agent such as tert-butyl nitrite, followed by a metal bromide such as copper (II) bromide. This bromination reaction may also be done after the amide is reduced (Step 5a of Scheme 4). Multiple bromination can occur in this process.

Step 5

(a) The amide is reduced with a reducing agent such as borane in an organic solvent such as THF at from 0° C. to reflux.

(b) If $R_1$ is H, the sulfonamide nitrogen may be substituted as described in Step 4 of Scheme 2.

(c) If $R_1$ is H and $R_2$ is H, the sulfonamide nitrogen may be sulfonylated with an alkyl or aryl sulfonyl chloride such as methanesulfonyl chloride in the presence of a base such as n-butyl lithium.

(d) If $R_2$ is H, the sulfonamide may be brominated by following the Step 4 (d) of Scheme 2.

(e) If $R_2$ is an amine, it may be acylated with an acid chloride in an organic solvent such as methylene chloride in the presence of a base such as pyridine at from 0° C. to room temperature. In addition, it may be brominated by following the Step 4 (d) of Scheme 2. The product is then reductively alkylated as described for Step 5 of Scheme 1 to give the final desired compound.

Scheme 5

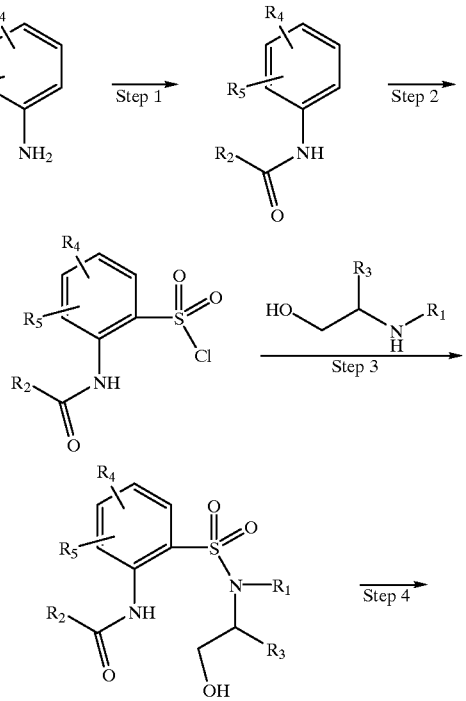

-continued

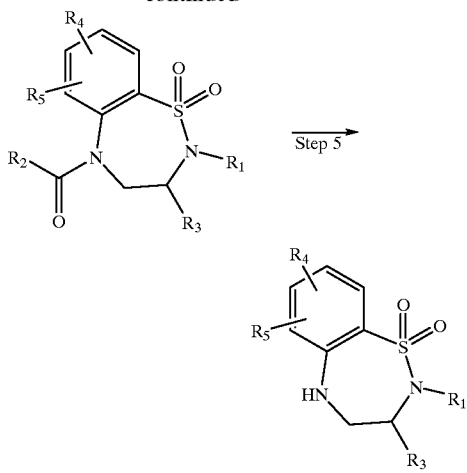

wherein $R_1$ and $R_2$ are selected from H, substituted alkyl, arylalkyl, aryl, heteroaryl; $R_3$ is selected from H, substituted alkyl, arylalkyl; $R_4$, $R_5$ are selected from H, halo, CN, alkyl, arylalkyl, aryl, heteroaryl or $R_4$ and $R_5$ may together to form a carbocyclic or heterocyclic ring.

Step 1

An aniline derivative is acylated with an anhydride such as trifluoroacetic anhydride in an organic solvent such as methylene chloride in the presence of a base such as pyridine at from 0° C. to room temperature.

Step 2

The amide is treated with a sulfonylating agent such as chlorosulfonic acid in an organic solvent such as chloroform at from about 0° C. to room temperature.

Step 3

The sulfonyl chloride is reacted with an optionally substituted aminoalcohol as described in Step 2 of Scheme 1.

Step 4

The resultant sulfonamide is cyclized by treatment with a dehydrating agent like DEAD/triphenylphosphine in an organic solvent such as THF.

Step 5

The amide is hydrolyzed by, for example, treatment with a base such as potassium carbonate in an organic solvent such as methanol. The product is then reductively alkylated as described for Step 5 of Scheme 1 to give the desired compound of formula I.

The invention will now be further described by the following working examples, which are preferred embodiments of the invention. All temperatures are in degrees Celsius (° C.) unless otherwise indicated. These examples are illustrative rather than limiting.

EXAMPLE 1

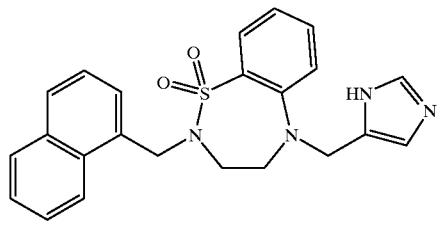

2,3,4,5-Tetrahydro-5-(1H-imidazol-4-ylmethyl)-2-(1-naphthalenylmethyl)-1,2,5-benzothiadiazepine, 1,1-dioxide, monohydrochloride A. N-1-[(1,1-Dimethylethoxy)-carbonyl]-N2-(1-naphthalenylmethyl)-diaminoethane To a stirred solution of mono-BOC-ethylene diamine (1.0 g, 6.25 mmol), 1-naphthaldehyde (0.9 mL, 6.63 mmol) and acetic acid (0.5 mL) in 50 mL of methanol at 0° C., was added sodium cyanoborohydride (NaCNBH$_3$, 500 mg, 7.8 mmol) in one portion. The mixture was stirred at 0° C. for 30 min. Saturated sodium hydrogen carbonate (NaHCO$_3$) solution was added and the mixture was concentrated under vacuum. The residue was partitioned between ethyl acetate and saturated NaHCO$_3$ solution. The organic layer was separated and dried over MgSO$_4$ and concentrated under vacuum to give Compound A as an oil.

B. N1-[(1,1-Dimethylethoxy)-carbonyl]-N2-(1-naphthalenylmethyl)-N2-(2-fluorobenzenesulfonyl)-diaminoethane To a stirred solution of Compound A (500 mg, 1.7 mmol) in methylene chloride (20 mL) and 1N aqueous NaOH solution (10 mL) at 0° C. was added 2-fluorobenzenesulfonyl chloride. The solution was stirred for 1 hour and acetic acid was added such that the aqueous layer was at pH 5.0. The organic layer was separated and the aqueous layer was extracted with methylene chloride (50 mL). The combined organic extracts were dried over MgSO$_4$ and concetrated under vacuum. The residue was purified by flash column chromatography (ethyl acetate/hexanes, 1:2) to give Compound B as a clear oil (450 mg, 59%). TLC R$_f$=0.25 (ethyl acetate, hexanes; 1:2).

C. N1-(1-naphthylmethyl)-N1-(2-fluoro-benzenesulfonyl)-diaminoethane

A solution of Compound B (450 mg, 1.0 mmol) in a mixture of trifluoroacetic aicd (TFA) and methylene chloride (3 mL/3 mL) at room temperature was stirred for 3 hours. The solvent was removed under vacuum and the residue was partitioned between saturated aqueous NaHCO$_3$ and ethyl acetate. The organic layer was separated, dried over MgSO$_4$ and concentrated under vacuum to give Compound C as an oil (300 mg, 84%). MS (M+H)$^+$ 359.

D. 2,3,4,5-Tetrahydro-2-(1-naphthalenylmethyl)-1,2,5-benzothiadiazepine, 1,1-dioxide A solution of Compound C (200 mg, 0.56 mmol) and potassium carbonate (K$_2$CO$_3$, 400 mg, 2.9 mmol) in DMF (3 mL) was heated at 105° C. for 18 hours. The mixture was partitioned between ethyl acetate and saturated NaHCO$_3$ solution. The organic layer was separated and washed with saturated ammonium chloride (NH$_4$Cl) and brine, dried over MgSO$_4$ and concentrated. The residue was purified by flash column chromtagraphy (ethyl acetate/hexanes, 1:2) to give Compound D as an oil (180 mg, 95%). TLC R$_f$=0.25; MS (M−H)$^−$ 377.

E. 2,3,4,5-Tetrahydro-5-(1H-imidazol-4-ylmethyl)-2-(1-naphthalenylmethyl)-1,2,5-benzothiadiazepine, 1,1-dioxide, monohydrochloride To a stirred solution of Compound D (170 mg, 0.50 mmol) and 4-formylimidazole (70 mg, 0.70 mmol) in a mixture of dichloroethane and acetic acid (3 mL, 2:1) was added sodium triacetoxyborohydride (NaBH(OAc)$_3$, 200 mg, 0.94 mmol). The mixture was stirred for 1 hour and diluted with 20 mL of ethyl acetate. Concentrated ammonium hydroxide (NH$_4$OH, 2 mL) solution was added and the mixture was stirred for 3 hours. The mixture was partitioned between ethyl acetate and saturated NaHCO$_3$ solution. The organic layer was separated and washed with saturated NH$_4$Cl solution and brine, dried over Na$_2$SO$_4$ and concentrated. The residue was dissolved in methanol, a solution of HCl in ether was added, the solvent was removed and the residue was triturated with ether to give Example 1 as a yellow solid [190 mg, 84%, mp: 128° C. (shrinks)].

MS (M+H)+ 419.

Analysis calculated for $C_{23}H_{22}N_4O_2S.1.1$ HCl.0.3 $H_2O.0.6$ $C_4H_{10}O$.

Calc'd: C, 60.00; H, 5.89; N, 11.02; S, 6.30; Cl, 7.67.
Found: C, 60.28; H, 5.51; N, 10.75; S, 6.42; Cl, 7.31.

EXAMPLE 2

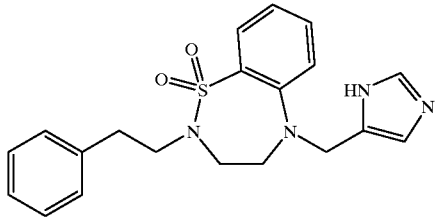

2,3,4,5-Tetrahydro-5-(1H-imidazol-4-ylmethyl)-2-(2-phenylethyl)-1,2,5-benzothiadiazepine, 1,1-dioxide, monohydrochloride A. N-2-Bromoethyl-2'-nitrobenzenesultonamide To a stirred solution at 0° C. of 2-nitrobenzenesulfonyl chloride (2.2 g, 10 mmol) in methylene chloride (50 mL) and aqueous NaHCO$_3$ solution (50 mL) was added bromoethylamine hydrobromide (4.1 g, 20 mmol). The mixture was stirred at 0° C. for 3 hours. The organic layer was separated and washed with 10% HCl solution and saturated NaHCO$_3$ solution, dried and concentrated to give Compound A as an oil (3.0 g, 97%).

B. 2,3,4,5-Tetrahydro-1,2,5-benzothiadiazepine, 1,1-dioxide

To a stirred solution of Compound A (3 g, 9.7 mmol) in ethyl acetate (100 mL) was added solid tin chloride dihydrate (SnCl$_2$.2H$_2$O, 7 g, 31.2 mmol). The mixture was stirred for 18 hours. A saturated solution of K$_2$CO$_3$ (4 mL) was added, followed by solid K$_2$CO$_3$ (10 g). The suspension was stirred for 3 hours and filtered. The filtrate was concentrated under vacuum to give N-2-bromoethyl-2'-aminobenzenesulfonamide, which is dissolved in ethanol (50 mL). This alcoholic solution was heated at reflux for 3 days. The solution was cooled and concentrated under vacuum to give Compound B as a solid (1.5 g, 78%).

C. 2,3,4,5-Tetrahydro-5-(1H-imidazol-4-ylmethyl)-2-(2-phenylethyl)-1,2,5-benzothiadiazepine, 1,1-dioxide To a stirred solution of Compound B (100 mg, 0.5 mmol) in 2 mL of anhydrous DMF in the presence of solid K$_2$CO$_3$ (300 mg, 2.2 mmol) and a catalytic amount of 18-crown-6 ether was added phenethyl bromide (90 µL, 0.66 mmol) via a syringe. The mixture was stirred at 60° C. for 18 hours and partitioned between ethyl acetate and saturated NH$_4$Cl solution. The organic layer was separated, washed with saturated NH$_4$Cl solution, dried over MgSO$_4$, and concentrated in vacuo. The residue was purified by column chromatography to give Compound C as a semisolid (95 mg, 63%). MS (M+H)+ 303.

D. 2,3,4,5-Tetrahydro-5-(1H-imidazol-4-ylmethyl)-2-(2-phenylethyl)-1,2,5-benzothiadiazepine, 1,1-dioxide, monohydrochloride Compound D was prepared as a yellow solid in 60% yield from Compound C as described for Compound E of Example 1. mp 95° C. (shrinks).

MS (M+H)+ 383

Analysis calculated for $C_{20}H_{22}N_4O_2S.1.5$ HCl.0.5 $H_2O.0.2$ $C_4H_{10}O$.

Calc'd: C, 54.19; H, 5.79; N, 12.16.
Found: C, 54.41; H, 5.41; N, 12.02.

EXAMPLE 3

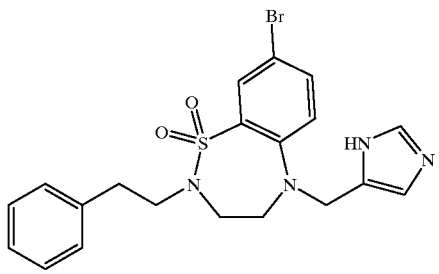

8-Bromo-2,3,4,5-tetrahydro-5-(1H-imidazol-4-ylmethyl)-2-(2-phenylethyl)-1,2,5-benzothiadiazepine, 1,1-dioxide, monohydrochloride A. 2,3,4,5-Tetrahydro-8-bromo-1,2,5-benzo-thiadiazepine, 1,1-dioxide To a stirred solution of Compound B of Example 2 (500 mg, 2.5 mmol) in a solvent mixture of acetic acid and DMF (5 mL, 1:1) was added bromine (120 µL, 2.4 mmol) via a syringe. The mixture was stirred for 30 minutes and partitioned between aqueous Na$_2$S$_2$O$_3$ solution (0.5N, 50 mL) and ethyl acetate (100 mL). The organic layer was separated and washed with brine (2×50 mL), dried over MgSO$_4$ and concentrated in vacuo to give Compound A as an oil (510 mg, 74%). TLC R$_f$=0.35 (ethyl acetate).

B. 8-Bromo-2,3,4,5-tetrahydro-5-(1H-imidazol-4-ylmethyl)-2-(2-phenylethyl)-1,2,5-benzothiadiazepine, 1,1-dioxide, monohydrochloride Compound B was prepared as a yellow solid from Compound A using the two step procedure described for Compound C of Example 2 and Compound E of Example 1. MS (M+H)+ 461

EXAMPLE 4

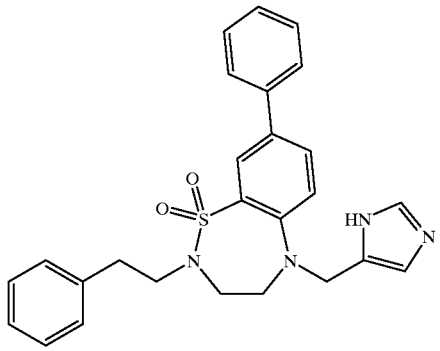

2,3,4,5-Tetrahydro-5-(1H-imidazol-4-ylmethyl)-8-phenyl-2-(2-phenylethyl)-1,2,5-benzothiadiazepine, 1,1-dioxide, monohydrochoride A. 2,3,4,5-Tetrahydro-8-phenyl-1,2,5-benzo-thiadiazepine, 1,1-dioxide To a solution of Compound A of Example 3 (20 mg, 0.05 mmol) in toluene (2 mL) and saturated NaHCO$_3$ solution (1 mL) was added a solution of phenylboronic acid (25 mg, 0.2 mmol) in ethanol (0.5 mL). The mixture was deaerated by argon, and tetrakis(triphenylphosphine) (Pd(Ph$_3$)$_4$, 3 mg) was added. The mixture was heated under argon at 100° C. for 5 hours, cooled to room temperature and partitioned between ethyl acetate and 1N NaOH solution. The organic layer was separated, washed with saturated NaHCO$_3$ and brine, dried and concentrated under vacuum. The residue was crystallized from methanol to give Compound A as a solid (16 mg, 80%), mp: 184–186° C. MS (M+H)+ 379.

B. 2,3,4,5-Tetrahydro-5-(1H-imidazol-4-ylmethyl)-8-phenyl-2-(2-phenylethyl)-1,2,5-benzothiadiazepine, 1,1-dioxide, monohydrochloride Compound B was prepared as a yellow solid from Compound A using the two step procedure described for Compound C of Example 2 and Compound E of Example 1. MS (M+H)+ 459

EXAMPLE 5

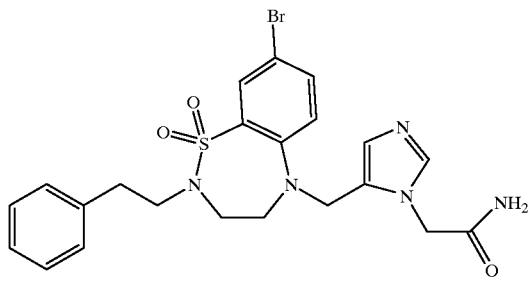

5-[[8-Bromo-2,3,4,5-tetrahydro-1,1-dioxo-2-(2-phenylethyl)-1,2,5-benzothiadiazepin-5-yl]methyl]-1H-imidazole-1-acetamide, monohydrochloride A. 8-Bromo-2,3,4,5-tetrahydro-5-(1-triphenylmethyl-imidazol-4-ylmethyl)-2-(2-phenylethyl)-1,2,5-benzothiadiazepine, 1,1-dioxide To a stirred solution of Example 3 (55 mg, 0.12 mmol) in pyridine (1 mL) at room temperature was added triphenylmethylchloride (37 mg, 0.13 mmol). The mixture was stirred for 3 days and partitioned between ethyl acetate and water. The organic layer was separated and washed with water and saturated NH₄Cl solution, dried over MgSO₄ and concentrated to afford Compound A. TLC R$_f$=0.20 (ethyl acetate).

B. 5-[[8-Bromo-2,3,4,5-tetrahydro-1,1-dioxo-2-(2-phenylethyl)-1,2,5-benzothiadiazepin-5-yl]methyl]-1H-imidazole-1-acetamide, monohydrochloride To a stirred solution of Compound A and diisopropylethylamine (21 µL, 0.12 mmol) in DMF (1 mL) was added iodoacetamide (25 mg, 0.14 mmol). The mixture was stirred for 2 days, cooled to 0° C. and triethylsilane (50 µL) and trifluoroacetic acid (0.5 mL) were added. The mixture was stirred at 0° C. for 30 minutes and partitioned between ethyl acetate and saturated NaHCO₃ solution. The organic layer was separated, dried over Na₂SO₄ and the residue was purified by column chromatography (methanol, ethyl acetate, methylene chloride, NH₄OH; 10%:25%:65%:0.5%; TLC R$_f$=0.25). The product was dissolved in methanol, ether solution of HCl was added, the solvent was removed to give a solid (7 mg, 11% for the 3 steps). MS (M+H)+ 518.

EXAMPLE 6

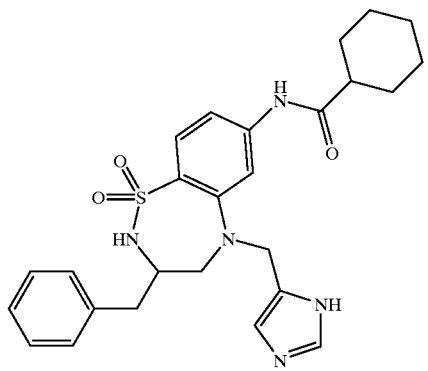

N-[2,3,4,5-Tetrahydro-5-(1H-imidazol-4-ylmethyl)-3-(phenylmethyl)-dioxide, monohydrochloride A. N-(2,4-Dinitrobenzenesulfonyl)-phenylalanine, methyl ester Compound A was prepared from phenylalanine methyl ester hydrochloride and 2,4-dinitrobenzenesulfonyl chloride as described for compound A of Example 2.

B. N-(2,4-Diaminobenzenesulfonyl)-phenylalanine, methyl ester

To a stirred solution of compound A (2.0 g, 4.9 mmol) in ethyl acetate was added SnCl₂.2H₂O (10 g, 44.3 mmol). The solution was stirred at room temperature for 18 hours. Saturated K₂CO₃ solution was added and the mixture was stirred 2 hours. Solid K₂CO₃ was added, the suspension was filtered, and the filtrate was concentrated to give compound A as an oil (1.4 g, 82%).

C. N-(2,4-Diaminobenzenesulfonyl)-phenylalanine

To a solution of compound B (1.6 g, 4.6 mmol) in THF-H₂O-MeOH (10:1:1) was added a solution of LiOH.H₂O (800 mg, 19.0 mmol) in water. The solution was stirred at room temperature for 18 hours. Acetic acid was added and the mixture was stirred 2 hours and concentrated. The residue was partitioned between ethyl acetate and 1% HCl solution. The aqueous layer was extracted with ethyl acetate and the combined organic extracts were dried over MgSO₄, and concentrated to give compound C as a solid (1.1 g, 71%, mp 182–183° C.).

D. 2,3,4,5-Tetrahydro-7-amino-4-oxo-3-phenylmethyl-1,2,5-benzothiadiazepine, 1,1-dioxide To a stirred solution of compound C (625 mg, 1.85 mmol) in 20 mL of anhydrous DMF in the presence of DIEA (0.4 mL, 2.26 mmol) was added Castro's reagent (1.0 g, 2.26 mmol) at 0° C. The mixture was stirred 30 minutes and the solvent was evaporated. The residue was partitioned between ethyl acetate and 1% HCl solution. The organic layer was washed with saturated NaHCO₃ solution, dried over MgSO₄ and concentrated. The residue was crystallized from MeOH to give compound D as a solid (450 mg, 79%, mp 243–245° C.)

E. 2,3,4,5-Tetrahydro-7-amino-3-phenylmethyl-1,2,5-benzothiadiazepine, 1,1-dioxide To a solution of compound D (350 mg, 1.1 mmol) in anhydrous THF at 0° C. under argon was added a solution of BH₃.THF. The mixture was stirred at 0° C. for 3 hours and at reflux for 3 hours. The mixture was allowed to cool to 0° C. and 15% HCl solution was added. The mixture was stirred at room temperature for 18 hour. A 5N NaOH solution was added to adjust to pH 11. The mixture was concentrated and the residue was partitioned between ethyl acetate and water. The organic layer was washed with saturated NH$_4$Cl solution, dried over MgSO$_4$ and concentrated to give compound E as an oil (250 mg, 77%). MS (ESI) (M+H)$^+$ 303.

F. N-[2,3,4,5-Tetrahydro-3-(phenylmethyl)-1,2,5-benzothiadiazepin-7-yl]cyclohexanecarboxamide, 1,1-dioxide To a solution of compound E (50 mg, 0.17 mmol) in methylene chloride in the presence of pyridine (14 μL, 0.17 mmol) at 0° C. was added cyclohexylcarbonyl chloride (23 μL, 0.17 mmol). The mixture was stirred for 30 minutes. Ether was added, and the resulting precipitate was collected and washed with ether to give compound F as a solid (15 mg, 22%).

G. N-[2,3,4,5-Tetrahydro-5-(1H-imidazol-4-ylmethyl)-3-(phenylmethyl)-1,2,5-benzothiadiazepin-7-yl] cyclohexanecarboxamide, 1,1-dioxide, monohydrochloride Compound G was prepared as a solid in 50% yield from Compound F as described for Compound E of Example 1, except that DMF was used as solvent. MS (ESI) (M+H)$^+$ 494.

EXAMPLE 7

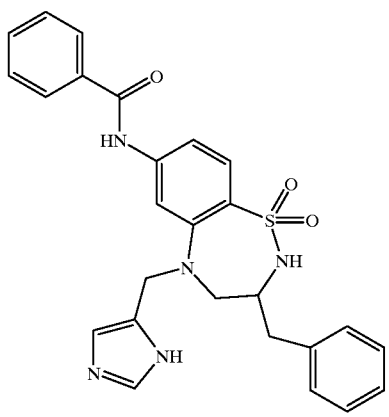

N-[2,3,4,5-Tetrahydro-5-(1H-imidazol-4-ylmethyl)-3-(phenylmethyl)-1,2,5-benzothiadiazepin-7-yl] phenylcarboxamide, 1,1-dioxide, monohydrochloride The title compound was prepared from benzoyl chloride as described in Example 6. MS (M+H)$^+$ 488.

EXAMPLE 8

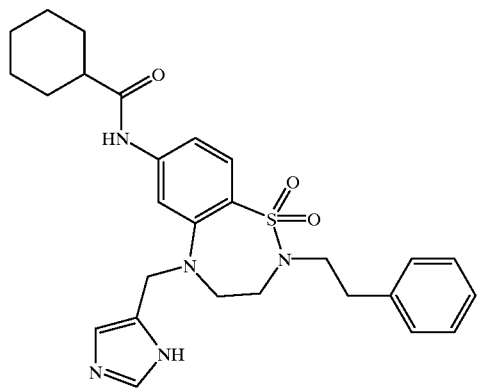

N-[2,3,4,5-Tetrahydro-5-(1H-imidazol-4-ylmethyl)-2-(phenylethyl)-1,2,5-benzothiadiazepin-7-yl] cyclohexanecarboxamide, 1,1-dioxide, monohydrochloride The title compound was prepared from N-phenethylglycine methyl ester as described in Example 6. MS (M+H)$^+$ 508.

EXAMPLE 9

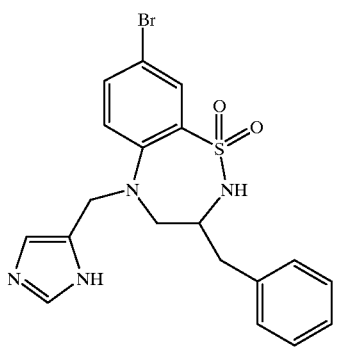

N-[2,3,4,5-Tetrahydro-8-bromo-5-(1H-imidazol-4-ylmethyl)-3-(phenylmethyl)-1,2,5-benzothiadiazepine, 1,1-dioxide, monohydrochloride A. 2,3,4,5-Tetrahydro-3-phenylmethyl-1,2,5-benzothiadiazepine, 1,1-dioxide The title compound was prepared from 2-nitrobenzenesulfonyl chloride and phenyl alanine methyl ester in the same manner as described for the preparation of compound A–E of Example 6. MS (M+H) 289.

B. 2,3,4,5-Tetrahydro-8-bromo-3-phenylmethyl-1,2,5-benzothiadiazepine, 1,1-dioxide To a stirred solution of compound A (3.02 g, 10.5 mmol) in chloroform at room temperature was added tetrabutyl ammonium tribromide (5.6 g, 12 mmol). The resultant mixture was stirred at room temperature for 30 min and partitioned between chloroform and aqueous sodium thiosulfate. The separated organic layer was washed with water, dried, and concentrated in vacuo. The resultant residue was purified by silica gel column chromatography (3:1, hexanes and ethyl acetate) to give the title compound as a solid (1.9 g, 50%). MS (M+H) 367.

C. N-[2,3,4,5-Tetrahydro-8-bromo-5-(1H-imidazol-4-ylmethyl)-3-(phenylmethyl)-1,2,5-benzothiadiazepine, 1,1-dioxide, monohydrochloride The title compound was prepared from compound B by following the procedure described for the preparation of compound E of Example 1. MS (M+H) 447; m. p. 180° C.

Anal. Calc'd for: $C_{19}H_{19}N_4O_2SBr.1.3HCl.0.50C_7H_8$ C, 49.97; H, 4.53; N, 10.36; S, 5.93; Br, 14.77.

Found: C, 49.72; H, 4.49; N, 10.15; S, 5.83; Br, 14.32.

EXAMPLE 10

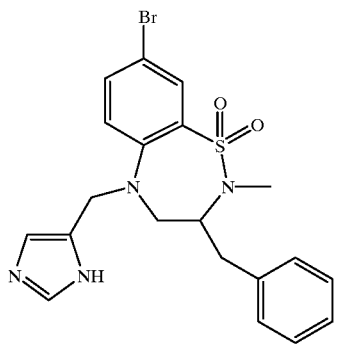

2,3,4,5-Tetrahydro-8-bromo-2-methyl-5-(1H-imidazol-4-ylmethyl)-3-(phenylmethyl)-1,2,5-benzothiadiazepine, 1,1-dioxide, monohydrochloride A. 2,3,4,5-Tetrahydro-8-bromo-2-methyl-3-phenylmethyl-1,2,5-benzothiadiazepine, 1,1-dioxide The title compound was prepared from compound B of Example 9 and methyl iodide by following the procedure described in the preparation of compound C of Example 2. MS (M+H) 382; m.p.192–193° C.

B. 2,3,4,5-Tetrahydro-8-bromo-2-methyl-5-(1H-imidazol-4-ylmethyl)-3-(phenylmethyl)-1,2,5-benzothiadiazepine, 1,1-dioxide, monohydrochloride The title compound was prepared from compound A by following the procedure described for preparation of compound E of Example 1. MS (M+H) 461; m.p. 140° C. Anal. calc'd for $C_{20}H_{21}N_4O_2SBr.HCl.0.50C_7H_8.1.5H_2O$:

C, 49.44; H, 5.12; N, 9.81; S, 5.62. Found: C, 49.37; H, 5.00; N, 9.42; S, 5.88.

EXAMPLE 11

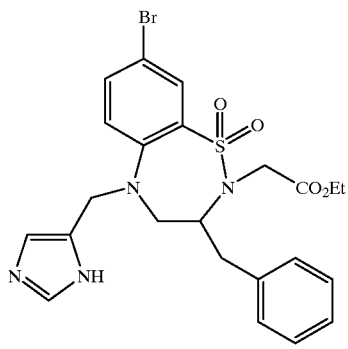

2,3,4,5-Tetrahydro-8-bromo-5-(1H-imidazol-4-ylmethyl)-3-(phenylmethyl)-1,2,5-benzothiadiazepine-2-acetic acid, ethyl ester, 1,1-dioxide, monohydrochloride A. 2,3,4,5-Tetrahydro-8-bromo-2-ethoxycarbonylmethyl-3-phenylmethyl-1,2,5-benzothiadiazepine, 1,1-dioxide The title compound was prepared from compound B of Example 9 and ethyl bromoacetate by following the procedure described in the preparation of compound C of Example 2. MS (M+H) 453; m.p. 68–70° C.

B. 2,3,4,5-Tetrahydro-8-bromo-5-(1H-imidazol-4-ylmethyl)-3-(phenylmethyl)-1,2,5-benzothiadiazepine-2-acetic acid, methyl ester, 1,1-dioxide, monohydrochloride The title compound was prepared from compound B by following the procedure described for preparation of compound E of Example 1. MS (M+H) 533. Anal. calc'd for $C_{23}H_{25}N_4O_4SBr.HCl.H_2O$:

C, 46.99; H, 4.80; N, 9.53; S, 5.45; Cl, 6.03; Br, 13.59.

Found: C, 47.08; H, 4.45; N, 8.95; S, 4.90; Cl, 4.89; Br, 13.63.

EXAMPLE 12

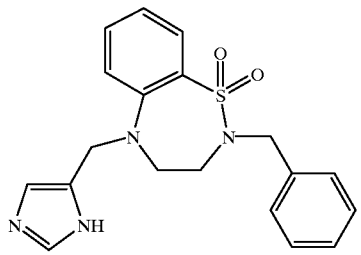

2,3,4,5-Tetrahydro-5-(1H-imidazol-4-ylmethyl)-2-phenylmethyl-1,2,5-benzothiadiazepine, 1,1-dioxide, monohydrochloride The title compound was prepared by following the procedures for the preparation of Example 2, except benzyl bromide was used in the place of phenethyl bromide in the preparation of compound C of Example 2. MS (M+H) 369.

EXAMPLE 13

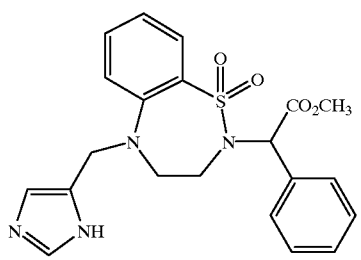

2,3,4,5-Tetrahydro-5-(1H-imidazol-4-ylmethyl)-a-phenyl-1,2,5-benzothiadiazepine-2-acetic acid, methyl ester, 1,1-dioxide, monohydrochloride The title compound was prepared by following the procedures for the preparation of Example 2, except methyl alfa-bromophenylacetate was used in the place of phenethyl bromide in the preparation of compound C of Example 2. MS (M+H) 413.

EXAMPLE 14

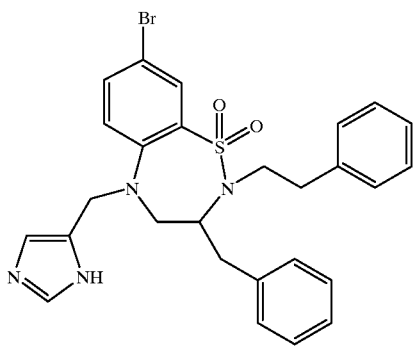

2,3,4,5-Tetrahydro-8-bromo-5-(1H-imidazol-4-ylmethyl)-2-(2-phenylethyl)-3-(phenylmethyl)-1,2,5-benzothiadiazepine, 1,1-dioxide, monohydrochloride The title compound was prepared by following the procedures for the preparation of Example 10, except phenethyl bromide was used in the place of methyl iodide in the preparation of compound A of Example 10. MS (M+H) 552.

EXAMPLE 15

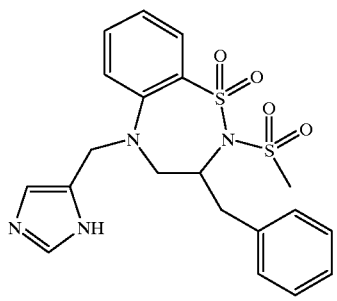

2,3,4,5-Tetrahydro-5-(1H-imidazol-4-ylmethyl)-2-(methylsulfonyl)-3-(phenylmethyl)-1,2,5-benzothiadiazepine, 1,1-dioxide, monohydrochloride A. 2,3,4,5-Tetrahydro-2-(methylsulfonyl)-3-phenylmethyl-1,2,5-benzothiadiazepine, 1,1-dioxide To a solution of 50 mg (0.174 mmol) of Compound A of Example 9 in 1 ml of THF, with ice cooling and under argon, was added dropwise 240 µl of 1.6M n-butyl lithium in hexane. To the resulting clear yellow solution was added dropwise 15 µl (0.19 mmol) of mesyl chloride. Stirring was continued with cooling for 1 hr, and then at rt for 1 hr. The mixture was evaporated to dryness and the residue diluted with ethyl acetate. The solution was washed once with water, dried (MgSO$_4$) and the solvent removed to afford an oil residue which crystallized. The crude product was subjected to flash chromatography on a 30 cc column of silica gel. Elution with chloroform afforded first, 25 mg (50%) of unreacted Compound A, followed by 28 mg (0.076 mmol, 44%) of Compound B as a white solid.

B. 2,3,4,5-Tetrahydro-5-(1H-imidazol-4-ylmethyl)-2-(methylsulfonyl)-3-(phenylmethyl)-1,2,5-benzothiadiazepine, 1,1-dioxide, monohydrochloride A solution of 25 mg (0.068 mmol) of Compound A and 13 mg (0.14 mmol) of 4-formylimidazole in 1 ml of methylene chloride and 0.5 ml of acetic acid was stirred at rt and under argon for 0.5 hr, after which time was added 30 mg (0.14 mmol) of sodium triacetoxyborohydride. Stirring was continued for 1 hr, after which time an additional 13 mg of 4-formylimidazole and 30 mg of sodium triacetoxy borohydride was added. Stirring was continued overnight. Additional portions of 4-formylimidazole and hydride were added after 15 hr, and again after 24 hr. The mixture was stirred overnight, evaporated to dryness and the residue diluted with ethyl acetate. Conc. ammonium hydroxide (5 ml) was added and the mixture stirred briefly. The aqueous layer was separated and the organic solution washed twice with brine, dried (MgSO$_4$) and the solvent removed to afford 28 mg of a solid foam, which was subjected to flash chromatography on a 30 cc column of silica gel. Elution with 5% methanol-chloroform afforded 21 mg of the free base of Compound C as a clear, colorless glass. The hydrochloride was prepared from this material by the addition of excess 1M HCl in ether to a solution of the free base in ethyl acetate. The resulting white precipitate was removed by filtration, dried (50° C., high vac, overnight) to afford 15 mg (0.031 mmole, 46%) of Example 15 as a white solid.

MS (M+H)$^+$: 447$^+$ $^{13}$C NMR (67.8 MHz, CD$_3$OD): δ36.2, 43.5, 46.6, 55.8, 63.9, 117.1, 117.8, 119.8, 127.0, 127.7, 128.8, 129.3, 130.3, 130.5, 133.8, 134.7, 138.3, 146.8.

EXAMPLE 16

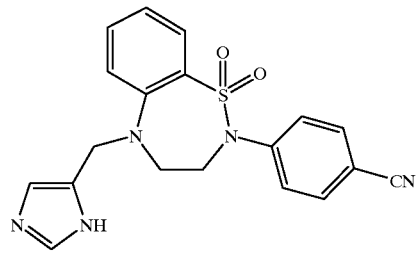

4-[2,3,4,5-Tetrahydro-5-(1H-imidazol-4-ylmethyl)-1,2,5-benzothiadiazepin-2-yl]benzonitrile, 1,1-dioxide, monohydrochloride A. 4-[2,3,4,5-Tetrahydro-1,2,5-benzothiadiazepin-2-yl]benzonitrile, 1,1-dioxide.

2,3,4,5-Tetrahydro-1,2,5-benzothiadiazepine, 1,1-dioxide (compound B of Example 2) was heated with 4-bromobenzonitrile in collidine in the presence of copper(I) oxide at 170° C. under argon for 18 h. The resultant mixture was partitioned between 10% aq. HCl solution and ethyl acetate. The organic layer was separated, dried over MgSO$_4$, and concentrated in vacuo. The residue was purified by silica gel column chromatography (1:1 hexanes and ethyl acetate) to give a solid (m.p. 71–73° C., 33% yield). MS (M+H) 300.

B. 4-[2,3,4,5-Tetrahydro-5-(1H-imidazol-4-ylmethyl)-1,2,5-benzothiadiazepin-2-yl]benzonitrile, 1,1-dioxide, monohydrochloride The title compound was prepared from compound A by following the procedure described for the preparation of compound E of Example 1. MS (M+H) 380.

TABLE 1

The Examples listed in Table 1 were prepared by following the procedure described for the preparation of the Example 16.

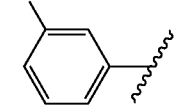

| | | R₁ | R₂ | MS (M + H) |
|---|---|---|---|---|
| Example 17 | 3-[2,3,4,5-Tetrahydro-5-(1H-imidazol-4-ylmethyl)-1,2,5-benzothiadiazepin-2-yl]benzonitrile, 1,1-dioxide, monohydrochloride | 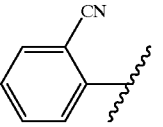 | H | 380 |
| Example 18 | 2-[2,3,4,5-Tetrahydro-5-(1H-Imidazol-4-ylmethyl)-1,2,5-benzothiadiazepin-2-yl]benzonitrile, 1,1-dioxide, monohydrochloride | 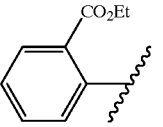 | H | 380 |
| Example 19 | 2-[2,3,4,5-Tetrahydro-5-(1H-Imidazol-4-ylmethyl)-1,2,5-benzothiadiazepin-2-yl]benzoic acid, ethyl ester, 1,1-dioxide, monohydrochloride | 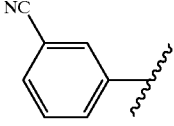 | H | 427 |
| Example 20 | 3-[8-Bromo-2,3,4,5-tetrahydro-5-(1H-imidazol-4-ylmethyl)-1,2,5-benzothiadiazepin-2-yl]benzonitrile, 1,1-dioxide, monohydrochloride | | Br | 458 |
| Example 21 | 2,3,4,5-Tetrahydro-5-(1H-imidazol-4-ylmethyl)-2-(2-thiazolyl)-1,2,5-benzothiadiazepine, 1,1-dioxide, monohydrochloride | 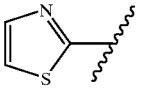 | H | 362 |
| Example 22 | 2,3,4,5-Tetrahydro-5-(1H-imidazol-4-ylmethyl)-2-(3-methoxyphenyl)-1,2,5-benzothiadiazepine, 1,1-dioxide, monohydrochloride | 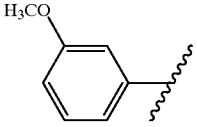 | H | 385 |
| Example 23 | 5-[2,3,4,5-Tetrahydro-5-(1H-imidazol-4-ylmethyl)-1,2,5-benzothiadiazepin-2-yl]-2-methoxy-N-methyl-N-(phenylmethyl)benzenesulfonamide, 1,1-dioxide, monohydrochloride | 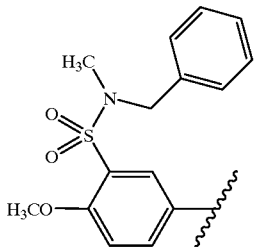 | H | 568 |

TABLE 1-continued

The Examples listed in Table 1 were prepared by following the procedure described for the preparation of the Example 16.

| | | $R_1$ | $R_2$ | MS (M + H) |
|---|---|---|---|---|
| Example 24 | 3-[2,3,4,5-Tetrahydro-5-(1H-imidazol-4-ylmethyl)-1,2,5-benzothiadiazepin-2-yl]benzoic acid, methyl ester, 1,1-dioxide, monohydrochloride | 3-($H_3CO_2C$)-phenyl | H | 413 |
| Example 25 | 2-[2,3,4,5-Tetrahydro-5-(1H-imidazol-4-ylmethyl)-1,2,5-benzothiadiazepin-2-yl)-N-methyl-N-(phenylmethyl)benzenesulfonamide, 1,1-dioxide, monohydrochloride | 2-(N-methyl-N-benzylsulfamoyl)phenyl | H | 538 |
| Example 26 | 2-[2,3,4,5-Tetrahydro-5-(1H-imidazol-4-ylmethyl)-1,2,5-benzothiadiazepin-2-yl]benzoic acid, ethyl ester, 1,1-dioxide, monohydrochloride | 2-($CO_2Et$)-phenyl | Br | 505 |
| Example 27 | 2-[2,3,4,5-Tetrahydro-5-(1H-imidazol-4-ylmethyl)-1,2,5-benzothiadiazepin-2-yl]-N-methyl-N-(phenylmethyl)benzamide, 1,1-dioxide, monohydrochloride | 2-(N-methyl-N-benzylcarbamoyl)phenyl | H | 502 |
| Example 28 | 2,3,4,5-Tetrahydro-5-(1H-imidazol-4-ylmethyl)-2-(2-methoxyphenyl)-1,2,5-benzothiadiazepine, 1,1-dioxide, monohydrochloride | 2-($OCH_3$)-phenyl | H | 385 |

TABLE 1-continued

The Examples listed in Table 1 were prepared by following the procedure described for the preparation of the Example 16.

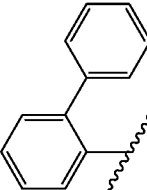

| | | R₁ | R₂ | MS (M + H) |
|---|---|---|---|---|
| Example 29 | 2,3,4,5-Tetrahydro-2-([1,1'-biphenyl]-2-yl)-5-(1H-imidazol-4-ylmethyl)-1,2,5-benzothiadiazepine, 1,1-dioxide, monohydrochloride | 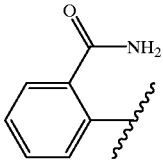 | H | 431 |
| Example 30 | 2-[2,3,4,5-Tetrahydro-5-(1H-imidazol-4-ylmethyl)-1,2,5-benzothiadiazepin-2-yl]benzamide, 1,1-dioxide, monohydrochloride | 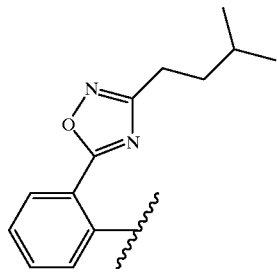 | H | 398 |
| Example 31 | 2,3,4,5-Tetrahydro-5-(1H-imidazol-4-ylmethyl)-2-[2-[3-(3-methylbutyl)-1,2,4-oxadiazol-5-yl]phenyl]-1,2,5-benzothiadiazepine, 1,1-dioxide, monohydrochloride | 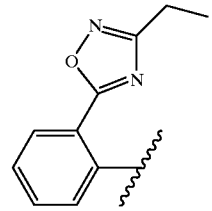 | H | 493 |
| Example 32 | 2,3,4,5-Tetrahydro-2-[2-(3-ethyl-1,2,4-oxadiazol-5-yl)phenyl]-5-(1H-imidazol-4-ylmethyl)-1,2,5-benzothiadiazepine, 1,1-dioxide, monohydrochloride | | H | 451 |
| Example 33 | 2,3,4,5-Tetrahydro-2-[2-(2-ethyl-1,3,4-oxadiazol-5-yl)phenyl]-5-(1H-imidazol-4-ylmethyl)-1,2,5-benzothiadiazepine, 1,1-dioxide, monohydrochloride | 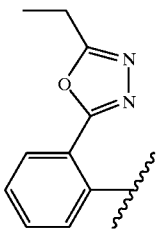 | H | 451 |

TABLE 1-continued

The Examples listed in Table 1 were prepared by following the procedure described for the preparation of the Example 16.

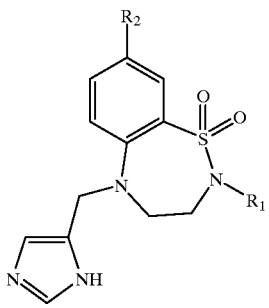

| | | R₁ | R₂ | MS (M + H) |
|---|---|---|---|---|
| Example 34 | 2,3,4,5-Tetrahydro-2-([1,1'-biphenyl]-2-yl)-8-bromo-5-(1H-imidazol-4-ylmethyl)-1,2,5-benzothiadiazepine, 1,1-dioxide, monohydrochloride | 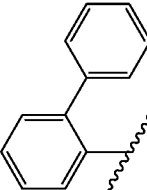 | Br | 509 |
| Example 35 | 2,3,4,5-Tetrahydro-5-(1H-imidazol-4-ylmethyl)-2-[2-(phenylmethoxy)phenyl]-1,2,5-benzothiadiazepine, 1,1-dioxide, monohydrochloride | 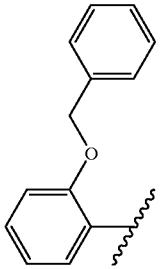 | H | 461 |
| Example 36 | 2,3,4,5-Tetrahydro-2-([1,1'-biphenyl]-2-yl)-5-(1H-imidazol-4-ylmethyl)-1,2,5-benzothiadiazepine-8-carbonitrile, 1,1-dioxide, monohydrochloride | 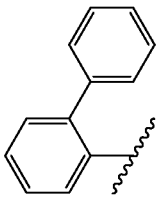 | CN | 456 |
| Example 37 | N-[[2,3,4,5-Tetrahydro-2-([1,1'-biphenyl]-2-yl)-5-(1H-imidazol-4-ylmethyl)-1,2,5-benzothiadiazepin-8-yl]methyl]acetamide, 1,1-dioxide, monohydrochloride | 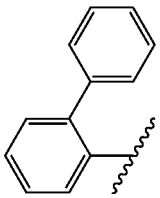 | 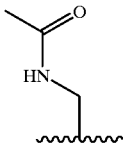 | 502 |
| Example 38 | 2-[2-[2,3,4,5-Tetrahydro-5-(1H-imidazol-4-ylmethyl)-1,2,5-benzothiadiazepin-2-yl]phenoxylbenzonitrile, 1,1-dioxide, monohydrochloride | 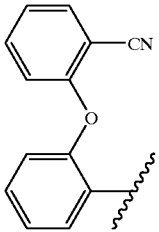 | H | 472 |

TABLE 1-continued

The Examples listed in Table 1 were prepared by following the procedure described for the preparation of the Example 16.

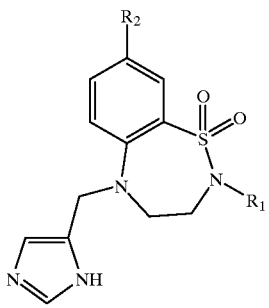

| | | R₁ | R₂ | MS (M + H) |
|---|---|---|---|---|
| Example 39 | 8-Bromo-2,3,4,5-tetrahydro-5-(1H-imidazol-4-ylmethyl)-2-[2-(phenylmethoxy)phenyl]-1,2,5-benzothiadiazepine, 1,1-dioxide, monohydrochloride | 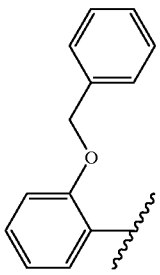 | Br | 539 |

TABLE 2

The Examples listed in Table 2 were prepared by following the procedures described in Schemes 4 and 5.

| | | Structure | MS (M + H) |
|---|---|---|---|
| Example 40 | 7-(Dimethylamino)-2,3,4,5-tetrahydro-5-(1H-imidazol-4-ylmethyl)-2-(2-phenylethyl)-1,2,5-benzothiadiazepine, 1,1-dioxide, monohydrochloride | 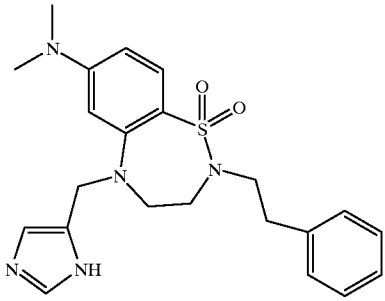 | 426 |
| Example 41 | 8-Bromo-7-(dimethylamino)-2,3,4,5-tetrahydro-5-(1H-imidazol-4-ylmethyl)-2-(2-phenylethyl)-1,2,5-benzothiadiazepine, 1,1-dioxide, monohydrochloride | 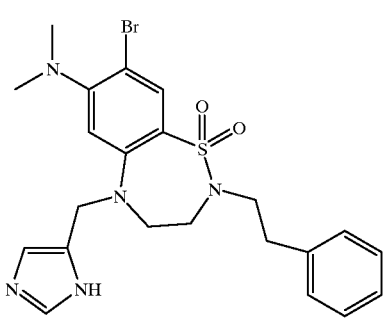 | 504 |

TABLE 2-continued

The Examples listed in Table 2 were prepared by following the procedures described in Schemes 4 and 5.

| | | Structure | MS (M + H) |
|---|---|---|---|
| Example 42 | 7-Bromo-2,3,4,5-tetrahydro-5-(1H-imidazol-4-ylmethyl)-2-(2-phenylethyl)-1,2,5-benzothiadiazepine, 1,1-dioxide, monohydrochloride | 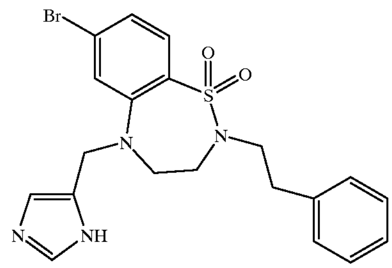 | 461 |
| Example 43 | 7,8-Dibromo-2,3,4,5-tetrahydro-5-(1H-imidazol-4-ylmethyl)-2-(2-phenylethyl)-1,2,5-benzothiadiazepine, 1,1-dioxide, monohydrochloride | 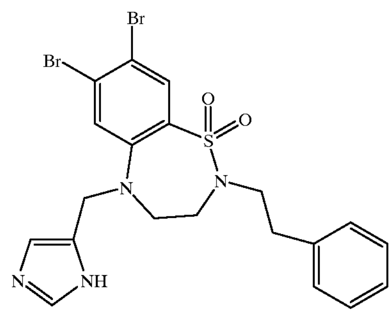 | 539 |
| Example 44 | 3,4,5,7,8,9-Hexahydro-5-(1H-imidazol-4-ylmethyl)-2-(2-phenylethyl)-2H-indeno[5,6-f]-1,2,5-thiadiazepine, 1,1-dioxide, monohydrochloride | 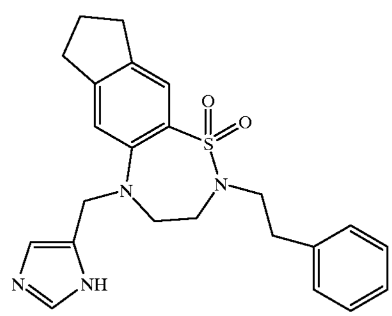 | 423 |
| Example 45 | N-[2-([1,1'-Biphenyl]-2-yl)-2,3,4,5-tetrahydro-5-(1H-imidazol-4-ylmethyl)-1,2,5-benzothiadiazepin-7-yl]acetamide, 1,1-dioxide, monohydrochloride | 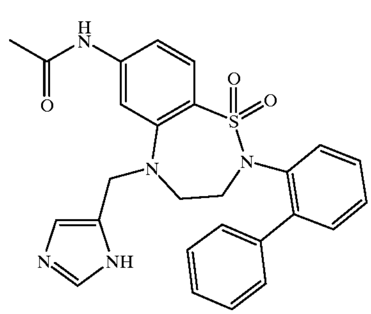 | 488 |

TABLE 2-continued

The Examples listed in Table 2 were prepared by following the procedures described in Schemes 4 and 5.

| | | Structure | MS (M + H) |
|---|---|---|---|
| Example 46 | 2-([1,1'-Biphenyl]-2-yl)-2,3,4,5-tetrahydro-5-(1H-imidazol-4-ylmethyl)-1,2,5-benzothiadiazepin-7-amine, 1,1-dioxide, monohydrochloride | 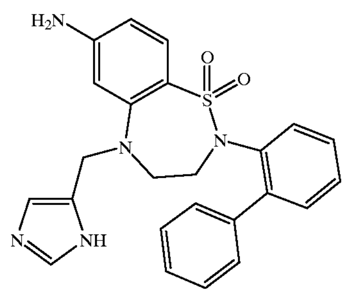 | 446 |
| Example 47 | 2-([1,1'-Biphenyl]-2-yl)-7,8-dibromo-2,3,4,5-tetrahydro-5-(1H-imidazol-4-ylmethyl)-1,2,5-benzothiadiazepine, 1,1-dioxide, monohydrochloride | 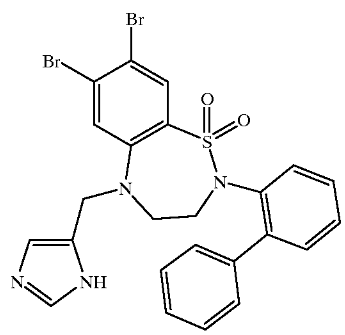 | 588 |
| Example 48 | 2-(3-Bromo[1,1'-Biphenyl]-2-yl)-7,8-dibromo-2,3,4,5-tetrahydro-5-(1H-imidazol-4-ylmethyl)-1,2,5-benzothiadiazepine, 1,1-dioxide, monohydrochloride | 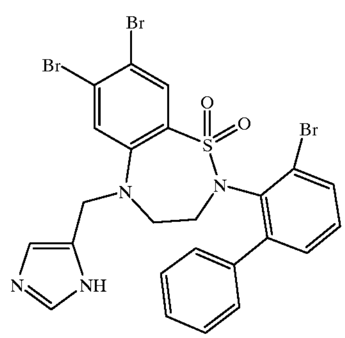 | 668 |
| Example 49 | 2-([1,1'-Biphenyl]-2-yl)-2,3,4,5-tetrahydro-N,5-bis(1H-imidazol-4-ylmethyl)-1,2,5-benzothiadiazepin-7-amine, 1,1-dioxide, monohydrochloride | 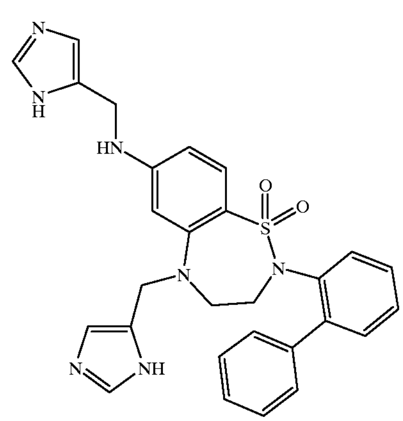 | 526 |

TABLE 2-continued

The Examples listed in Table 2 were prepared by following the procedures described in Schemes 4 and 5.

| | | Structure | MS (M + H) |
|---|---|---|---|
| Example 50 | 8-Bromo-4,5-dihydro-5-(1H-imidazol-4-ylmethyl)-N-methyl-N,3-bis(phenylmethyl)-1,2,5-benzothiadiazepine-2(3H)-acetamide, 1,1-dioxide, monohydrochloride | 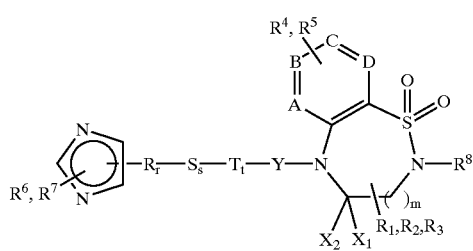 | 608 |

What is claimed:

1. A compound of the formula

I $$\text{(structure shown)}$$

or enantiomers, diastereomers, pharmaceutically acceptable salts, prodrugs, or solvates thereof wherein:

$R^1$, $R^2$, $R^8$, and $R^{13}$ are hydrogen, alkyl, substituted alkyl, alkenyl, substituted alkenyl, alkynyl, substituted alkynyl, aralkyl, cycloalkyl, aryl, substituted aryl, heterocyclo, or substituted heterocyclo provided that if $R^8$ is a substituted alkyl, the substiuent is not imidazolyl;

$R^4$, $R^5$ are hydrogen, halo, nitro, cyano, or U-$R^{13}$;

$R^6$, $R^7$, $R^9$, $R^{10}$, $R^{11}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are hydrogen, lower alkyl, or substituted alkyl;

$R^{12}$ is hydrogen, lower alkyl, aryl, substituted alkyl, or aryl;

A, B, C, and D are carbon, or nitrogen;

R, S, and T are $CH_2$, CO, or $CH(CH_2)_pQ$, wherein Q is $NR^{26}R^{27}$ or $OR^{28}$;

U is sulfur, oxygen, $NR^{14}$, CO, SO, $SO_2$, $CO_2$, $NR^{15}CO_2$, $NR^{16}CONR^{17}$, $NR^{18}SO_2$, $NR^{19}SO_2NR^{20}$, $SO_2NR^{21}$, $NR^{22}CO$, $CONR^{23}$, $PO_2R^{24}$, or $PO_3R^{25}$ or U is absent;

$X_1$ and $X_2$ are independently oxygen, hydrogen, $R^1$, or $R^2$;

Y is $CHR^9$, $SO_2$, CO, $CO_2$, O, $NR^{10}$, $SO_2NR^{11}$, or $CONR^{12}$;

r, s and t are 0 or 1; and p is 0, 1, or 2;

with the proviso that $R^{13}$ may be hydrogen except when U is SO, $SO_2$, $NR^{15}CO_2$, or $NR^{18}SO_2$.

2. A compound of claim 1 wherein each of A, B, C, and D is carbon.

3. A compound selected from the group consisting of:

2,3,4,5-Tetrahydro-5-(1H-imidazol-4-ylmethyl)-2-(1-naphthalenylmethyl)-1,2,5-benzothiadiazepine, 1,1-dioxide, monohydrochloride;

2,3,4,5-Tetrahydro-5-(1H-imidazol-4-ylmethyl)-2-(2-phenylethyl)-1,2,5-benzothiadiazepine, 1,1-dioxide, monohydrochloride;

8-Bromo-2,3,4,5-tetrahydro-5-(1H-imidazol-4-ylmethyl)-2-(2-phenylethyl)-1,2,5-benzothiadiazepine, 1,1-dioxide, monohydrochloride;

2,3,4,5-Tetrahydro-5-(1H-imidazol-4-ylmethyl)-8-phenyl-2-(2-phenylethyl)-1,2,5-benzothiadiazepine, 1,1-dioxide, monohydrochloride;

5-[[8-Bromo-2,3,4,5-tetrahydro-1,1-dioxo-2-(2-phenylethyl)-1,2,5-benzothiadiazepin-5-yl]methyl]-1H-imidazole-1-acetamide, monohydrochloride;

N-[2,3,4,5-Tetrahydro-5-(1H-imidazol-4-ylmethyl)-3-(phenylmethyl)-1,2,5-benzothiadiazepin-7-yl] cyclohexanecarboxamide, 1,1-dioxide, monohydrochloride;

N-[2,3,4,5-Tetrahydro-5-(1H-imidazol-4-ylmethyl)-3-(phenylmethyl)-1,2,5-benzothiadiazepin-7-yl] phenylcarboxamide, 1,1-dioxide, monohydrochloride;

N-[2,3,4,5-Tetrahydro-5-(1H-imidazol-4-ylmethyl)-2-(phenylethyl)-1,2,5-benzothiadiazepin-7-yl] cyclohexanecarboxamide, 1,1-dioxide, monohydrochloride;

N-[2,3,4,5-Tetrahydro-8-bromo-5-(1H-imidazol-4-ylmethyl)-3-(phenylmethyl)-1,2,5-benzothiadiazepine, 1,1-dioxide, monohydrochloride;

2,3,4,5-Tetrahydro-8-bromo-2-methyl-5-(1H-imidazol-4-ylmethyl)-3-(phenylmethyl)-1,2,5-benzothiadiazepine, 1,1-dioxide, monohydrochloride;

2,3,4,5-Tetrahydro-8-bromo-5-(1H-imidazol-4-ylmethyl)-3-(phenylmethyl)-1,2,5-benzothiadiazepine-2-acetic acid, ethyl ester, 1,1-dioxide, monohydrochloride;

2,3,4,5-Tetrahydro-5-(1H-imidazol-4-ylmethyl)-2-phenylmethyl-1,2,5-benzothiadiazepine, 1,1-dioxide, monohydrochloride;

2,3,4,5-Tetrahydro-5-(1H-imidazol-4-ylmethyl)-a-phenyl-1,2,5-benzothiadiazepine-2-acetic acid, methyl ester, 1,1-dioxide, monohydrochloride;

2,3,4,5-Tetrahydro-8-bromo-5-(1H-imidazol-4-ylmethyl)-2-(2-phenylethyl)-3-(phenylmethyl)-1,2,5-benzothiadiazepine, 1,1-dioxide, monohydrochloride;

2,3,4,5-Tetrahydro-5-(1H-imidazol-4-ylmethyl)-2-(methylsulfonyl)-3-(phenylmethyl)-1,2,5-benzothiadiazepine, 1,1-dioxide, monohydrochloride;

4-[2,3,4,5-Tetrahydro-5-(1H-imidazol-4-ylmethyl)-1,2,5-benzothiadiazepin-2-yl]benzonitrile, 1,1-dioxide, monohydrochloride;

3-[2,3,4,5-Tetrahydro-5-(1H-imidazol-4-ylmethyl)-1,2,5-benzothiadiazepin-2-yl]benzonitrile, 1,1-dioxide, monohydrochloride;

2-[2,3,4,5-Tetrahydro-5-(1H-imidazol-4-ylmethyl)-1,2,5-benzothiadiazepin-2-yl]benzonitrile, 1,1-dioxide, monohydrochloride;

2-[2,3,4,5-Tetrahydro-5-(1H-imidazol-4-ylmethyl)-1,2,5-benzothiadiazepin-2-yl]benzoic acid, ethyl ester, 1,1-dioxide, monohydrochloride;

3-[8-Bromo-2,3,4,5-tetrahydro-5-(1H-imidazol-4-ylmethyl)-1,2,5-benzothiadiazepin-2-yl]benzonitrile, 1,1-dioxide, monohydrochloride;

2,3,4,5-Tetrahydro-5-(1H-imidazol-4-ylmethyl)-2-(2-thiazolyl)-1,2,5-benzothiadiazepine, 1,1-dioxide, monohydrochloride;

2,3,4,5-Tetrahydro-5-(1H-imidazol-4-ylmethyl)-2-(3-methoxyphenyl)-1,2,5-benzothiadiazepine, 1,1-dioxide, monohydrochloride;

5-[2,3,4,5-Tetrahydro-5-(1H-imidazol-4-ylmethyl)-1,2,5-benzothiadiazepin-2-yl]-2-methoxy-N-methyl-N-(phenylmethyl)benzenesulfonamide, 1,1-dioxide, monohydrochloride;

3-[2,3,4,5-Tetrahydro-5-(1H-imidazol-4-ylmethyl)-1,2,5-benzothiadiazepin-2-yl]benzoic acid, methyl ester, 1,1-dioxide, monohydrochloride;

2-[2,3,4,5-Tetrahydro-5-(1H-imidazol-4-ylmethyl)-1,2,5-benzothiadiazepin-2-yl]-N-methyl-N-(phenylmethyl)benzenesulfonamide, 1,1-dioxide, monohydrochloride;

2-[2,3,4,5-Tetrahydro-5-(1H-imidazol-4-ylmethyl)-1,2,5-benzothiadiazepin-2-yl]benzoic acid, ethyl ester, 1,1-dioxide, monohydrochloride;

2-[2,3,4,5-Tetrahydro-5-(1H-imidazol-4-ylmethyl)-1,2,5-benzothiadiazepin-2-yl]-N-methyl-N-(phenylmethyl)benzamide, 1,1-dioxide, monohydrochloride;

2,3,4,5-Tetrahydro-5-(1H-imidazol-4-ylmethyl)-2-(2-methoxyphenyl)-1,2,5-benzothiadiazepine, 1,1-dioxide, monohydrochloride;

2,3,4,5-Tetrahydro-2-([1,1'-biphenyl]-2-yl)-5-(1H-imidazol-4-ylmethyl)-1,2,5-benzothiadiazepine, 1,1-dioxide, monohydrochloride;

2-[2,3,4,5-Tetrahydro-5-(1H-imidazol-4-ylmethyl)-1,2,5-benzothiadiazepin-2-yl]benzamide, 1,1-dioxide, monohydrochloride;

2,3,4,5-Tetrahydro-5-(1H-imidazol-4-ylmethyl)-2-[2-[3-(3-methylbutyl)-1,2,4-oxadiazol-5-yl]phenyl]-1,2,5-benzothiadiazepine, 1,1-dioxide, monohydrochloride;

2,3,4,5-Tetrahydro-2-[2-(3-ethyl-1,2,4-oxadiazol-5-yl)phenyl]-5-(1H-imidazol-4-ylmethyl)-1,2,5-benzothiadiazepine, 1,1-dioxide, monohydrochloride;

2,3,4,5-Tetrahydro-2-[2-(2-ethyl-1,3,4-oxadiazol-5-yl)phenyl]-5-(1H-imidazol-4-ylmethyl)-1,2,5-benzothiadiazepine, 1,1-dioxide, monohydrochloride;

2,3,4,5-Tetrahydro-2-([1,1'-biphenyl]-2-yl)-8-bromo-5-(1H-imidazol-4-ylmethyl)-1,2,5-benzothiadiazepine, 1,1-dioxide, monohydrochloride;

2,3,4,5-Tetrahydro-5-(1H-imidazol-4-ylmethyl)-2-[2-(phenylmethoxy)phenyl]-1,2,5-benzothiadiazepine, 1,1-dioxide, monohydrochloride;

2,3,4,5-Tetrahydro-2-([1,1'-biphenyl]-2-yl)-5-(1H-imidazol-4-ylmethyl)-1,2,5-benzothiadiazepine-8-carbonitrile, 1,1-dioxide, monohydrochloride;

N-[[2,3,4,5-Tetrahydro-2-([1,1'-biphenyl]-2-yl)-5-(1H-imidazol-4-ylmethyl)-1,2,5-benzothiadiazepin-8-yl]methyl]acetamide, 1,1-dioxide, monohydrochloride;

2-[2-[2,3,4,5-Tetrahydro-5-(1H-imidazol-4-ylmethyl)-1,2,5-benzothiadiazepin-2-yl]phenoxy]benzonitrile, 1,1-dioxide, monohydrochloride;

8-Bromo-2,3,4,5-tetrahydro-5-(1H-imidazol-4-ylmethyl)-2-[2-(phenylmethoxy)phenyl]-1,2,5-benzothiadiazepine, 1,1-dioxide, monohydrochloride;

7-(Dimethylamino)-2,3,4,5-tetrahydro-5-(1H-imidazol-4-ylmethyl)-2-(2-phenylethyl)-1,2,5-benzothiadiazepine, 1,1-dioxide, monohydrochloride;

8-Bromo-7-(dimethylamino)-2,3,4,5-tetrahydro-5-(1H-imidazol-4-ylmethyl)-2-(2-phenylethyl)-1,2,5-benzothiadiazepine, 1,1-dioxide, monohydrochloride;

7-Bromo-2,3,4,5-tetrahydro-5-(1H-imidazol-4-ylmethyl)-2-(2-phenylethyl)-1,2,5-benzothiadiazepine, 1,1-dioxide, monohydrochloride;

7,8-Dibromo-2,3,4,5-tetrahydro-5-(1H-imidazol-4-ylmethyl)-2-(2-phenylethyl)-1,2,5-benzothiadiazepine, 1,1-dioxide, monohydrochloride;

3,4,5,7,8,9-Hexahydro-5-(1H-imidazol-4-ylmethyl)-2-(2-phenylethyl)-2H-indeno[5,6-f]-1,2,5-thiadiazepine, 1,1-dioxide, monohydrochloride;

N-[2-([1,1'-Biphenyl]-2-yl)-2,3,4,5-tetrahydro-5-(1H-imidazol-4-ylmethyl)-1,2,5-benzothiadiazepin-7-yl]acetamide, 1,1-dioxide, monohydrochloride;

2-([1,1'-Biphenyl]-2-yl)-2,3,4,5-tetrahydro-5-(1H-imidazol-4-ylmethyl)-1,2,5-benzothiadiazepin-7-amine, 1,1-dioxide, monohydrochloride;

2-([1,1'-Biphenyl]-2-yl)-7,8-dibromo-2,3,4,5-tetrahydro-5-(1H-imidazol-4-ylmethyl)-1,2,5-benzothiadiazepine, 1,1-dioxide, monohydrochloride;

2-(3-Bromo[1,1'-Biphenyl]-2-yl)-7,8-dibromo-2,3,4,5-tetrahydro-5-(1H-imidazol-4-ylmethyl)-1,2,5-benzothiadiazepine, 1,1-dioxide, monohydrochloride;

2-([1,1'-Biphenyl]-2-yl)-2,3,4,5-tetrahydro-N,5-bis(1H-imidazol-4-ylmethyl)-1,2,5-benzothiadiazepin-7-amine, 1,1-dioxide, monohydrochloride; and 8-Bromo-4,5-dihydro-5-(1H-imidazol-4-ylmethyl)-N-methyl-N,3-bis(phenylmethyl)-1,2,5-benzothiadiazepine-2(3H)-acetamide.

4. A method of inhibiting farnesyl protein transferase which comprises administering to a mammalian subject in need thereof an effective amount of a compound of claim 1.

5. A method of inhibiting prenyl transferases which comprises administering to a mammalian subject in need thereof an effective amount of a compound of claim 1.

6. A method of inhibiting tumors having a high incidence of ras involvement which comprises administering to a mammalian subject in need thereof an effective amount of a compound of claim 1.

7. A method of claim 6 wherein the tumors are of the colon, lung, pancreas, or in which prenyl transferase contributes to tumor maintenance, growth, or development.

* * * * *